US010210949B2

(12) United States Patent
Twitchell, Jr. et al.

(10) Patent No.: US 10,210,949 B2
(45) Date of Patent: *Feb. 19, 2019

(54) SELECTIVE ACCESS TO MEDICAL SYMPTOM TRACKING DATA USING DISPERSIVE STORAGE AREA NETWORK (SAN)

(71) Applicant: DISPERSIVE NETWORKS INC., Cumming, GA (US)

(72) Inventors: Robert W. Twitchell, Jr., Cumming, GA (US); Thomas Andrew Dawson, Aldershot (GB)

(73) Assignee: DISPERSIVE NETWORKS, INC., Alpharetta, GA (US)

( * ) Notice: Subject to any disclaimer, the term of this patent is extended or adjusted under 35 U.S.C. 154(b) by 427 days.

This patent is subject to a terminal disclaimer.

(21) Appl. No.: 14/833,829

(22) Filed: Aug. 24, 2015

(65) Prior Publication Data

US 2016/0085917 A1    Mar. 24, 2016

Related U.S. Application Data

(63) Continuation of application No. 13/361,943, filed on Jan. 30, 2012, now Pat. No. 9,116,734, which is a
(Continued)

(51) Int. Cl.
*G06F 9/455* (2018.01)
*G16H 10/60* (2018.01)
(Continued)

(52) U.S. Cl.
CPC ....... *G16H 10/60* (2018.01); *G06F 17/30312* (2013.01); *G06F 17/30386* (2013.01); *G06F 19/00* (2013.01); *H04L 67/1097* (2013.01)

(58) Field of Classification Search
CPC ............. G06F 19/322; G06F 17/30312; G06F 17/30386; H04L 67/1097
See application file for complete search history.

(56) References Cited

U.S. PATENT DOCUMENTS 3,668,644 A * 6/1972 Looschen ............... G11C 29/74
365/200
4,375,678 A * 3/1983 Krebs, Jr. ............... G11C 29/74
365/189.04
(Continued)

*Primary Examiner* — Adam Lee
(74) *Attorney, Agent, or Firm* — Tillman Wright, PLLC; Chad D. Tillman; Jeremy C. Doerre

(57) ABSTRACT

A method of monitoring symptoms of a person includes repeating, over a period of time, the steps of: selecting, by the person, one or more symbolic representations corresponding to one or more symptoms from a predefined set of symbolic representations presented to the person; and electronically recording data regarding the one or more symbolic representations selected by the person such that the data is electronically accessible later for generating a history of the symptoms of the person over the period of time. The data is transferred over virtual networks using virtual dispersive routing and stored in dispersive storage area networks (SANs). The data is classified as trusted, corrupted, invalid or uncertain, and/or as trusted, ambiguous and inadequate.

18 Claims, 12 Drawing Sheets

Related U.S. Application Data continuation-in-part of application No. 13/360,739, filed on Jan. 28, 2012, now abandoned, which is a continuation-in-part of application No. 13/007,595, filed on Jan. 14, 2011, now Pat. No. 8,560,634, which is a continuation-in-part of application No. 12/499,075, filed on Jul. 7, 2009, now Pat. No. 8,593,098, which is a continuation-in-part of application No. 12/253,926, filed on Oct. 17, 2008, now Pat. No. 7,895,348.

(60) Provisional application No. 61/462,055, filed on Jan. 28, 2011, provisional application No. 61/462,055, filed on Jan. 28, 2011, provisional application No. 61/133,935, filed on Jul. 7, 2008, provisional application No. 60/999,603, filed on Oct. 17, 2007.

(51) Int. Cl.
*G06F 17/30* (2006.01)
*H04L 29/08* (2006.01)
*G06F 19/00* (2018.01)

(56) References Cited

U.S. PATENT DOCUMENTS

| | | | | |
|---|---|---|---|---|
| 4,916,608 | A * | 4/1990 | Shultz | G06F 9/5016 711/203 |
| 7,406,407 | B2 * | 7/2008 | Larus | G06F 9/5077 703/27 |
| 7,586,915 | B1 * | 9/2009 | Indiresan | H04L 12/4645 370/392 |
| 8,141,090 | B1 * | 3/2012 | Graupner | G06F 9/45558 709/225 |
| 2004/0081105 | A1 * | 4/2004 | Shimazaki | H04L 41/00 370/254 |
| 2005/0108709 | A1 * | 5/2005 | Sciandra | G06F 9/505 718/1 |
| 2007/0038998 | A1 * | 2/2007 | Fries | G06F 9/45537 718/1 |
| 2007/0300220 | A1 * | 12/2007 | Seliger | G06F 8/61 718/1 |
| 2008/0172448 | A1 * | 7/2008 | Wonus | G06F 9/4416 709/203 |
| 2008/0209429 | A1 * | 8/2008 | Van Riel | G06F 9/505 718/104 |
| 2008/0256536 | A1 * | 10/2008 | Zhao | G06F 9/45537 718/1 |

\* cited by examiner

Touch sensitive areas of the display for indicating intensity or degree of symptom Touch sensitive areas of the display for indicating intensity or degree of symptom Touch sensitive areas of the display for
indicating intensity or degree of symptom Touch sensitive areas of the display for
indicating intensity or degree of symptom symptoms generally unwell fatigue motivation sleep problems cough URTI (upper respiratory tract infection)

injury muscle pain abdominal problems other

Notes:

SELECTIVE ACCESS TO MEDICAL SYMPTOM TRACKING DATA USING DISPERSIVE STORAGE AREA NETWORK (SAN)

CROSS-REFERENCE TO RELATED APPLICATION

The present application is a U.S. continuation patent application of, and claims priority under 35 U.S.C. § 120 to, U.S. nonprovisional patent application Ser. No. 13/361,943, filed Jan. 30, 2012, which '943 application is a U.S. nonprovisional patent application of, and claims priority under § 119(e) to, U.S. provisional patent application Ser. No. 61/462,055, filed Jan. 28, 2011, and which '943 application is a U.S. continuation-in-part patent application of, and claims priority under 35 U.S.C. § 120 to, U.S. nonprovisional patent application Ser. No. 13/360,739, filed Jan. 28, 2012,
(1) which '739 application is a U.S. nonprovisional patent application of, and claims priority under § 119(e) to, U.S. provisional patent application Ser. No. 61/462,055, filed Jan. 28, 2011, and
(2) which '739 application is a continuation-in-part patent application of, and claims priority under 35 U.S.C. § 120 to, U.S. nonprovisional patent application Ser. No. 13/007,595, filed Jan. 14, 2011, which '595 application published as U.S. patent application publication no. 2011/0179136 on Jul. 21, 2011, and which '595 application is a continuation-in-part patent application of, and claims priority under 35 U.S.C. § 120 to, U.S. nonprovisional patent application Ser. No. 12/499,075, filed Jul. 7, 2009, which '075 application published as U.S. patent application publication no. 2010/0009758 on Jan. 14, 2010, and
(a) which '075 application is a continuation-in-part patent application of, and claims priority under 35 U.S.C. § 120 to, U.S. nonprovisional patent application Ser. No. 12/253,926, filed Oct. 17, 2008, which '926 application published as U.S. patent application publication no. 2009/0106439 on Apr. 23, 2009, and
   (i) which '926 application is a nonprovisional patent application of, and claims priority under 35 U.S.C. § 119(e) to U.S. provisional patent application Ser. No. 60/999,603, filed Oct. 17, 2007, and
   (ii) which '926 application is a nonprovisional patent application of, and claims priority under 35 U.S.C. § 119(e) to U.S. provisional patent application Ser. No. 61/133,935, filed Jul. 7, 2008, and
(b) which '075 application is a nonprovisional patent application of, and claims priority under 35 U.S.C. § 119(e) to U.S. provisional patent application Ser. No. 61/133,935, filed Jul. 7, 2008.

The disclosure of each of the priority applications, any publications thereof, and any patents issuing therefrom, is incorporated by reference herein. Moreover, the principal disclosure of provisional patent application Ser. No. 61/462,055 is contained in the Appendix hereof, which is incorporated by reference herein.

COPYRIGHT STATEMENT

All of the material in this patent document is subject to copyright protection under the copyright laws of the United States and other countries. The copyright owner has no objection to the facsimile reproduction by anyone of the patent document or the patent disclosure, as it appears in official governmental records but, otherwise, all other copyright rights whatsoever are reserved.

BACKGROUND OF THE INVENTION

The healthcare industry is undergoing transformational change with a massive drive for standardized communication systems, robust security, improved efficiency, and increased accountability. In addition to this, there have been major and rapid advances in medical sensing and mobile communications devices with advances in functionality coupled with improvements in portability (miniaturization and power efficiency). There have also been unprecedented advances in objective technologies across the board and specialties, especially in the areas of imaging and laboratory analysis.

While such advances have been going on, this technical culture has effectively neglected the most important reason for medical presentation and intervention, i.e., the stories as told by the patients. Indeed, clinical professors universally reinforce the importance of patient history in medical monitoring and diagnosis. Medical history is acknowledged by most healthcare professionals to supersede the importance of examination, imaging, and laboratory investigations. Without an accurate recall and transcription of events, the accuracy of medical diagnosis can be critically compromised. For example, an individual who is breathing with difficulty, and is red and blotchy and cannot remember eating a peanut thirty minutes earlier, will compromise a physician's diagnosis of a nut allergy and may lead to the individual not avoiding nuts and having the same potentially life-threatening problem in the future.

In addition, physicians rely on patient feedback on efficacy of interventions, reporting of adverse effects, and progression of disease. Due to treatment and individual variability (resulting from a myriad of factors including genetics, nutrition, lifestyle, and history), the response to any one intervention is variable and, thus, feedback is extremely important. For the treating physician, monitoring this response occurs mainly at the post-prescription appointment. This can be problematic because there can be a significant delay or error in reporting adverse effects, or lack of efficacy, due to elapsed time between appointments, thereby resulting in decreased likelihood of an accurate recall of events.

This reliance on "the individual's story" is of significant importance because it likely relates directly to the problem that precipitated the person's visit to the health care provider. There are, however, problems with this reliance on doctor/patient communication, as human memory is fallible, and there can be variable delays between reporting and the actual time of the course of events leading up to the appointment. It is well established that recall of events can be inaccurate, and this is even more of an issue in certain medical conditions, such as a head injury. As well as memory, bias at the time of any professional consultation due to literacy, general communication skills, language barriers, cultural barriers, ethnic barriers, and socioeconomic barriers also impede effective communications between individuals and their medical healthcare providers.

In addition to the above, there are potentially multiple transcription errors at the healthcare provider level from other factors including preconception, leading and closing questioning, time pressure, and general misunderstanding. There is fallibility of conventional healthcare provider/patient communications.

Some tools have been developed to address the foregoing foreseen deficiencies in the current healthcare paradigm, but they generally require a reasonably high degree of literacy to make full use of such tools. Exemplary tools are disclosed, for example, in U.S. Pat. No. 6,529,195 and U.S. Pat. No. 6,856,315, each of which is incorporated herein by reference for disclosure of such tools. For example, body image mapping has been used for tracking pain; and pictorial charts have been used for depicting symptoms to identify infections or asthma.

Nonetheless, it is believed that no one has used representations of symptoms in an on-screen format that actually depict how the symptoms feel; enable the assignment to symptoms of values (including binary values, ranges, measures, and intensities); and/or associated the symptoms with time thereof and/or special (geographical) location thereof; and then entered such data into electronic health records for the purposes of clinical decision making.

One or more of these unique benefits and advantages are provided in accordance with one or more aspects and features of the present invention. Indeed, it is believed that one or more aspects and features address current limitations in the widespread usability of technologies, including: user input, which generally requires some knowledge of how to use the technologies with keyboard entry; instructions and guidance, which utilizes written text, thus failing to be usable by those with disabilities or language difficulties; and the lack of decision making based on patient stories being built into current clinical decision making applications.

As will be appreciated from the disclosure below, one or more aspects and features of the invention solves problems of communicating, translating and transcribing. This especially applies to those persons who are otherwise limited in the way they can communicate using language, ether verbal or written/typed. Indeed, many aspects and features of the invention are patient-centric and empower individuals, and populations of individuals, in communicating their stories, giving voice to their experiences of symptoms over time and enhancing medical decision making based thereon.

SUMMARY OF THE INVENTION

The present invention generally relates to systems, apparatus, and methods pertaining to medical data acquisition and storage and, more particularly, to the monitoring, storage and access to medical data pertaining to symptoms experienced by people. Furthermore, some aspects and features of the invention generally revolve around tracking symptoms utilizing desktop or mobile hardware and software for input through a variety of user interfaces.

The present invention includes many aspects and features. Moreover, while many aspects and features relate to, and are described in, the context of symptom tracking, analysis, and decision making based at least in part thereon, one or more aspects of the present invention are not limited to such use only. Indeed, some aspects are applicable without regard to the context or type of data that is acquired, while some aspects relate to a language agnostic system for communicating and recording medical symptoms with temporal and spatial coordinates for enhancing medical audit, decision-making, and support, as will become apparent from the following summaries and detailed descriptions of aspects, features, and one or more embodiments of the present invention.

In an aspect of the present invention, a communications system utilizes symbology—or icon-based communications—coupled with single words, or simple phrases, in one or more languages for tracking and monitoring symptoms. When used on mobile communications devices, subjective experiences can be recorded in, or near to, real-time, thereby addressing another communication issue, that of memory. In features of this aspect, intensity of the symptom is recorded and the time and geolocation information are recorded in conjunction with the identification of the symptom being experienced.

In an aspect of the invention a method of monitoring one or more symptoms of a person comprises repeating, over a period of time, the steps of: (a) selecting, by the person, one or more symbolic representations corresponding to one or more symptoms from a predefined set of symbolic representations presented to the person; and (b) electronically recording data regarding the one or more symbolic representations selected by the person such that the data is electronically accessible later for generating a history of the symptoms of the person over the period of time.

In a feature of the invention, the one or more symbolic representations corresponding to one or more symptoms is selected using an electronic device comprising a component for displaying the predefined set of symbolic representations that is coupled to a user input for receiving the selection of the one or more symbolic representations by the person. The electronic device may be operable by voice; operable by gestures; operable by recognition of facial expressions of a person; operable by recognition of eye movements of a person; operable by touch; operable by brain activity; operable by brain activity using magnetic sensors; operable by brain activity using electric sensors; or any combination of the foregoing.

In another feature, the electronic device includes a piezoelectric component for creating heat. The electronic device creates heat such that virtual Braille functionality is provided. Preferably, the electronic device generates heat in distinct and separate locations of the electronic device so as to be operable by visually impaired persons.

In another feature, the method further comprises the steps of electronically communicating the recorded data to a healthcare provider.

In another feature, the method further comprises the steps of electronically communicating the recorded data to cloud-based data storage.

In another feature, the one or more symbolic representations of the predefined set comprise illustrations of complex facial expressions.

In another feature, the one or more symbolic representations of the predefined set comprises illustrations of separate body regions.

In another feature, the one or more symbolic representations of the predefined set comprise separate anatomical structures.

In another feature, the two or more symbolic representations of the predefined set comprise different colors.

In another feature, the one or more symbolic representations of the predefined set comprise simple language identifiers. Each simple language identifier may consists of no more than a single word; may consist of no more than two words; may comprise words of different languages; and may comprises two phrases, each in a different language.

In another feature, one or more of the symbolic representations of the predefined set comprise intensity ratings or ranges.

In another feature, the one or more symbolic representations of the predefined set comprises two illustrations representing extremes and a bridge extending there between representative of a range between the extremes.

In another feature, the predefined set of symbolic representations further includes a symbolic representation of a normal state of the person.

In another feature, the predefined set of symbolic representations further includes a symbolic representation of a happy state of the person.

In another feature, the predefined set of symbolic representations further includes a symbolic representation of a healthy state of the person.

In another feature, the history of the symptoms of the person over the period of time comprises a chronological history of the symptoms of the person during the period of time.

In another feature, the history of the symptoms of the person over the period of time comprises a spatial representation of the locations of the selections of the symptoms by the person during the period of time.

In another feature, the history of the symptoms of the person over the period of time comprises both a chronological history of the selections of the symptoms by the person during the period of time, and a spatial representation of the locations of the selections of the symptoms of the person during the period of time.

In another feature, data regarding the one or more symbolic representations selected by the person includes an identification of the corresponding one or more selected symptoms.

In another feature, the data regarding the one or more symbolic representations selected by the person includes a timestamp for when the one or more symbolic representations were selected.

In another feature, the data regarding the one or more symbolic representations selected by the person includes an identification of the location at which the one or more symbolic representations were selected. The identification of the location at which the one or more symbolic representations were selected may include GPS coordinates of the location at which the one or more symbolic representations were selected.

In another feature, the data regarding the one or more symbolic representations that were selected includes an indication of the intensity of a symptom for which a symbolic representation was selected.

In another feature, the data regarding the one or more symbolic representations that were selected includes a numerical representation of a range of a symptom for which a symbolic representation was selected. The numerical representations of ranges of the symptom may be applied in one of four dimensions for graphically illustrating the symptoms of the person, with one of the four dimensions being time.

In another feature, the predefined set of symbolic representations are presented to the person by way of a display.

In another feature, the predefined set of symbolic representations are presented to the person by being displayed on a touch screen.

In another feature, the step of electronically recording data regarding the one or more symbolic representations selected by the person comprises recording data in an electronic device of the person. The data regarding the one or more symbolic representations selected by the person may be recorded in an electronic device that is carried by the person, and the electronic device may communicate wirelessly with other electronic devices.

In another feature, the one or more symbolic representations corresponding to one or more symptoms is selected using a mobile device.

In another feature, the one or more symbolic representations corresponding to one or more symptoms is selected using a smart phone.

In another feature, the one or more symbolic representations corresponding to one or more symptoms is selected using a laptop.

In another feature, the one or more symbolic representations corresponding to one or more symptoms is selected using a tablet computer.

In another feature, the one or more symbolic representations corresponding to one or more symptoms is selected using a public computer.

In another feature, the one or more symbolic representations corresponding to one or more symptoms is selected using a personal computer.

In another feature, the one or more symbolic representations corresponding to one or more symptoms is selected using an Internet enable television.

In another feature, the step of electronically recording data regarding the one or more symbolic representations selected by the person comprises electronically communicating the data from an electronic device at which the selection is made to one or more other electronic devices for safekeeping of the data. The other electronic device may comprise one or more servers; one or more other computers; or combination thereof. Additionally, electronically communicating may occur over a communications network; over the Internet; wirelessly; over a cellular network; via TCP/IP communications; or any combination thereof.

In another feature, the step of electronically recording data regarding the one or more symbolic representations selected by the person comprises electronically communicating the data from an electronic device at which a selection is made by the person to cloud based storage.

In another feature, the step of electronically recording data regarding the one or more symbolic representations selected by the person comprises recording the data in an electronic healthcare record of the person.

In another feature, the period of time is the time between visits by the person to a healthcare provider.

In another feature, the period of time is the time between visits by the person to a healthcare clinic.

In another feature, the period of time is the time between visits by the person to an automated healthcare station. The automated healthcare station may comprise a booth at a pharmacy and, more specifically, may comprise a booth at a pharmacy whereat a person's blood pressure is automatically taken.

In another feature, the period of time is the time between visits by the person to a laboratory.

In another feature, the period of time is the time between laboratory testing.

In another feature, the period of time is the time between blood tests.

In another feature, the period of time is the time between blood glucose tests.

In another feature, the period of time is the time between self-administered tests.

In another feature, the data is electronically accessible by a healthcare professional for generating a history of one or more of the symptoms that were selected by the person over the period of time. The history of the one or more symptoms that were selected may be used in making a clinical decision regarding the provision of healthcare to the person. The clinical decision may be made by a healthcare professional, and the clinical decision may be automatically made using software.

In another feature, the data is electronically accessible by a researcher for generating a history of one or more of the symptoms that were selected by the person over the period of time.

In another feature, the data is electronically accessible by the person for generating a history of one or more of the symptoms that were selected by the person over the period of time.

In another feature, the data is electronically accessible and is used to facilitate self, professional or automated decision making, support, audit, or guidance.

In another feature, the data regarding the one or more symbolic representations selected by the person comprises a personal alphanumeric identifier of the person.

In another feature, an avatar of the person is updated based on the data regarding the one or more symbolic representations selected by the person.

In another feature, an avatar of the person is updated based on the data regarding the one or more symbolic representations selected by the person, and wherein the avatar is associated with a website.

In another feature, an avatar of the person is updated based on the data regarding the one or more symbolic representations selected by the person, and wherein the avatar is associated with a social networking website.

In another feature, an avatar of the person is updated based on the data regarding the one or more symbolic representations selected by the person, and wherein the avatar is associated with an instant messaging program.

In another feature, an avatar of the person is updated based on the data regarding the one or more symbolic representations selected by the person, and wherein the avatar is associated with twitter.

In another feature, an avatar of the person is updated based on the data regarding the one or more symbolic representations selected by the person, and wherein the avatar is associated with facebook.

In another feature, an avatar of the person is updated based on the data regarding the one or more symbolic representations selected by the person, and wherein the avatar is associated with a blogs.

In another feature, the data regarding the one or more symbolic representations selected by the person does not comprise a personal identifier of the person.

In another feature, the method further comprises accessing the data regarding the one or more symbolic representations selected by the person and compiling a history based on the accessed data.

In another feature, the method further comprises accessing the data regarding the one or more symbolic representations selected by the person and compiling a history based on the accessed data.

In another feature, the method further comprises accessing the data regarding the one or more symbolic representations selected by the person and making a clinical decision based, in part, on indications of the intensity of the one or more symptoms selected.

In another feature, the method further comprises accessing the data regarding the one or more symbolic representations selected by the person and making a clinical decision based, in part, on changes in indications of the intensity of the one or more symptoms over a temporal sequence.

In another feature, the method further comprises accessing the data regarding the one or more symbolic representations selected by the person and making a clinical decision based, in part, on changes in indications of the intensity of the one or more symptoms over a spatial sequence.

In another feature, the method further comprises accessing the data regarding the one or more symbolic representations selected by the person and making a clinical decision based, in part, on the accessed data in relation to past and/or current medical history data of the person.

In another feature, the method further comprises accessing the data regarding the one or more symbolic representations selected by the person and making a clinical decision based, in part, on the accessed data in relation to family medical history data of the person.

In another feature, the method further comprises accessing the data regarding the one or more symbolic representations selected by the person and making a clinical decision based, in part, on the accessed data in relation to past food and beverage intake data of the person.

In another feature, the method further comprises accessing the data regarding the one or more symbolic representations selected by the person and making a clinical decision based, in part, on the accessed data in relation to past and/or current social history data of the person.

In another feature, the method further comprises accessing the data regarding the one or more symbolic representations selected by the person and making a clinical decision based, in part, on the accessed data in relation to past and/or current retail and consumer history data of the person.

In another feature, the method further comprises accessing the data regarding the one or more symbolic representations selected by the person and making a clinical decision based, in part, on the accessed data in relation to past and/or current prescription drug data of the person.

In another feature, the method further comprises accessing the data regarding the one or more symbolic representations selected by the person and making a clinical decision based, in part, on the accessed data in relation to past and/or current over the counter medication data of the person.

In another feature, the method further comprises accessing the data regarding the one or more symbolic representations selected by the person and making a clinical decision based, in part, on the accessed data in relation to past and/or current recreational drug use data of the person.

In another feature, the method further comprises accessing the data regarding the one or more symbolic representations selected by the person and making a clinical decision based, in part, on the accessed data in relation to past and/or current alcohol and tobacco consumption history data of the person.

In another feature, the method further comprises accessing the data regarding the one or more symbolic representations selected by the person and making a clinical decision based, in part, on the accessed data in relation to past and/or current travel history data of the person.

In another feature, the method further comprises accessing the data regarding the one or more symbolic representations selected by the person and making a clinical decision based, in part, on the accessed data in relation to past and/or current accommodation history data of the person.

In another feature, the method further comprises accessing the data regarding the one or more symbolic representations selected by the person and making a clinical decision based, in part, on the accessed data in relation to past and/or current conventional and complementary medicine intervention history data of the person.

In another feature, the method further comprises accessing the data regarding the one or more symbolic representations selected by the person and making a clinical decision based, in part, on the accessed data in relation to past and/or current exercise and activity history of the person.

In another feature, the method further comprises accessing the data regarding the one or more symbolic representations selected by the person and making a clinical decision based, in part, on the accessed data in relation to past and/or current exercise and activity history data of the person.

In another feature, the method further comprises the steps of accessing the data regarding the one or more symbolic representations selected by the person and displaying the accessed data over time in the nature of a movie.

In another feature, the method further comprises the steps of accessing the data regarding the one or more symbolic representations selected by the person and displaying the accessed data over time in the nature of a graph.

In another feature, the method further comprises the steps of accessing the data regarding the one or more symbolic representations selected by the person and displaying the accessed data on a map.

In another feature, the method further comprises the steps of accessing the data regarding the one or more symbolic representations selected by the person and comparing the data to predefined diagnostic datasets for determining likely diagnosis of the selected symptoms of the person.

In another aspect of the invention, a method of monitoring one or more symptoms of a plurality of persons comprises: (a) repeating, for each person over a respective period of time for that person, the steps of (i) selecting, by that person, one or more symbolic representations corresponding to one or more symptoms from a predefined set of symbolic representations presented to that person, and (ii) electronically recording data regarding the one or more symbolic representations selected by that person; and (b) electronically accessing the data electronically recorded for generating a history of the symptoms of a subset of the plurality of persons over a selected period of time overlapping with the respective periods of time of the persons of the subset.

In a feature, the plurality of persons comprise a predefined group of people. The predefined group of people may be of the same culture; may be of the same socioeconomic status; may have the same learning difficulties; may be persons with high risks of one or more particular healthcare issues. Generally, the persons preferably share one or more common characteristics. Moreover, the recorded data may include information regarding the person for which the data is recorded; any may include a unique identifier of the person for which the data is recorded or, alternatively, include a non-unique identifier of the person for which the data is recorded. In a feature, the data recorded includes general profile information regarding the person for which the data is recorded, and the subset of the plurality of persons is determined based at least in part on the general profile information of those persons.

In another feature, the history of the symptoms of each person over the respective period of time for each person comprises a chronological history of the symptoms of each person during the respective period of time.

In another feature, the history of the symptoms of each person over the respective period of time for each person comprises a spatial representation of the locations of the selections of the symptoms by each person during the respective period of time.

In another feature, the history of the symptoms of each person over the respective period of time for each person comprises both a chronological history of the symptoms of each person during the respective period of time, and a spatial representation of the locations of the selections of the symptoms by each person during the respective period of time.

In another feature, data regarding the one or more symbolic representations selected by each person includes an identification of the corresponding one or more selected symptoms.

In another feature, the data regarding the one or more symbolic representations selected by each person includes a timestamp for when the one or more symbolic representations were selected.

In another feature, the data regarding the one or more symbolic representations selected by each person includes an identification of the location at which the one or more symbolic representations were selected. The identification of the location at which the one or more symbolic representations were selected by each person may include GPS coordinates of the location at which the one or more symbolic representations were selected.

In another feature, the data regarding the one or more symbolic representations that were selected by each person includes an indication of the intensity of a symptom for which a symbolic representation was selected.

In another feature, the information is electronically accessible by a researcher for generating a history of one or more of the symptoms that were selected by the plurality of persons.

In another feature, the information is electronically accessible by the person for generating a history of one or more of the symptoms that were selected by the plurality of persons.

In another feature, the information is electronically accessible and is used to facilitate self, professional or automated decision making, support, audit, or guidance.

In another feature, the method further comprises accessing the data regarding the one or more symbolic representations selected by the plurality of persons and compiling a history based on the accessed data.

In another feature, the method further comprises the steps of accessing the data regarding the one or more symbolic representations selected by the plurality of persons and displaying the accessed data over time in the nature of a movie.

In another feature, the method further comprises the steps of accessing the data regarding the one or more symbolic representations selected by the plurality of persons and displaying the accessed data over time in the nature of a graph.

In another feature, the method further comprises the steps of accessing the data regarding the one or more symbolic representations selected by the plurality of persons and displaying the accessed data on a map.

In another feature, the method further comprises accessing the data regarding the one or more symbolic representations selected by the plurality of persons, identifying past and current community history of the symptoms selected, and making a clinical decision based, in part, on the past and current community history data of the plurality of persons.

In another aspect, an apparatus used in monitoring one or more symptoms of a person comprises: (a) a display for presenting to the person one or more symbolic representations corresponding to one or more symptoms from a predefined set of symbolic representations; (b) a user input for receiving a selection by the person of one or more symbolic representations of the predefined set; (c) machine readable medium for electronically recording data regarding one or more symbolic representations selected by the person over a period of time; (d) a processor; and (e) computer readable instructions contained in computer readable medium which, when executed by the processor, perform a method of monitoring one or more symptoms of a person, the method comprising repeating, over a period of time, the steps of: (i) presenting on the display the one or more symbolic representations from the predefined set of symbolic representations; (ii) receiving a selection by the person of one or more symbolic representations of the predefined set; and (iii) electronically recording in the machine readable medium data regarding one or more symbolic representations selected by the person over the period of time.

In a feature, the data is recorded such that the data is electronically accessible later for generating a history of the symptoms of the person over the period of time.

In another feature, the display and the user input are components of a touch screen.

In another feature, the apparatus further comprises a communications component by which the recorded data is communicated from the apparatus to another device whereat a history is generated of the symptoms of the person over the period of time.

In another feature, the apparatus further comprises a wireless communications component by which the recorded data is communicated from the apparatus to another device whereat a history is generated of the symptoms of the person over the period of time. The wireless communications component may comprise an RF radio component including a transceiver.

In another feature, the apparatus is handheld and portable.

In another feature, the apparatus further comprises a consumer electronic device.

In another feature, the apparatus further comprises a handheld consumer electronic device.

In another aspect of the invention, a system for monitoring one or more symptoms of a plurality of persons comprises: (a) a plurality of computing devices each used by a respective person whose symptoms are monitored, each computing device comprising, (i) a display configured to present to the respective person one or more symbolic representations corresponding to one or more symptoms from a predefined set of symbolic representations, (ii) a user input configured to receive a selection by the respective person of one or more symbolic representations of the predefined set, (iii) a communications component configured to communicate data regarding one or more symbolic representations selected by the respective person; and (b) one or more computing devices configured to, (i) receive the communicated data from the plurality of computing devices of the persons, and (ii) store the received data such that the data is accessible later for processing of the data.

In another feature, one of the computing devices of a respective one of the persons is configured to electronically access the stored data and process the accessed data for generating a history of symptoms of the respective person.

In another feature, the system further comprises a plurality of computing devices each configured to (i) electronically access the stored data, and (ii) process the accessed data for generating a history of symptoms of one or more of the plurality of persons.

In another feature, the system further comprises a plurality of computing devices each configured to (i) electronically access the stored data, and (ii) process the accessed data for generating a history of symptoms of the plurality of persons. One of the computing devices configured to electronically access the stored data and process the accessed data for generating a history of symptoms may be used by a healthcare professional.

In another feature, one or more of the computer devices of the persons comprise machine readable medium configured to electronically record for later communication a sequence of data regarding one or more symbolic representations selected over a period of time.

In another feature, the communicated data is received over a communications network.

In another feature, the computing devices of the persons are configured to communicate the data using the TCP/IP protocol.

In another feature, the computing devices of the persons are configured to communicate the data over the Internet.

In another feature, the one or more computer devices configured to receive and store the data comprise a server.

In another feature, the one or more computer devices configured to receive and store the data comprise a plurality of servers.

In another aspect, a system for monitoring one or more symptoms of a plurality of persons comprises: (a) a plurality of consumer electronic devices, each used by a respective person whose symptoms are monitored, each consumer electronic device comprising (i) a display configured to present to the respective person one or more symbolic representations corresponding to one or more symptoms from a predefined set of symbolic representations, (ii) a user input configured to receive a selection by the respective person of one or more symbolic representations of the predefined set, (iii) a communications component configured to communicate data regarding one or more symbolic representations selected by the respective person; and (b) one or more storage devices configured to, (i) receive the communicated data from the plurality of computing devices of the persons, and (ii) store the received data such that the data is accessible later for processing of the data; and (c) a plurality of computing devices each configured to, (i) electronically access the stored data, and (ii) process the accessed data for generating a history of symptoms of the plurality of persons.

In additional aspects and features of the invention, data is transferred over virtual networks as disclosed in the incorporated documents; data is stored in dispersed storage area network as disclosed in the incorporated documents; data is stored and accessed in dispersed storage area network utilizing virtual dispersive routing (VDR), as disclosed in the incorporated documents; decision support is enhanced by classifying data as being trusted, corrupted, invalid or uncertain; and decision support is enhanced by classifying datasets as trusted, ambiguous and inadequate, where ambiguous data may contain corrupted or invalid data points.

In addition to the aforementioned aspects and features of the present invention, it should be noted that the present invention further encompasses the various possible combinations and subcombinations of such aspects and features. Thus, for example, any aspect may be combined with an aforementioned feature in accordance with the present invention without requiring any other aspect or feature.

BRIEF DESCRIPTION OF THE DRAWINGS

One or more preferred embodiments of the present invention now will be described in detail with reference to the accompanying drawings, wherein the same elements are referred to with the same reference numerals.

FIG. 4a through FIG. 4b and FIG. 5a through FIG. 5c each illustrates additional exemplary symbolic representations of symptoms, each of which could be included in a predefined set for presenting to a user for selection, and each of which includes a range by which a user can select an intensity of the symptom felt when selecting the symptom.

FIG. 6a illustrates the receipt of a plurality of data streams from each of a plurality of devices that portions of data are stored on.

DETAILED DESCRIPTION

Figure 1A:
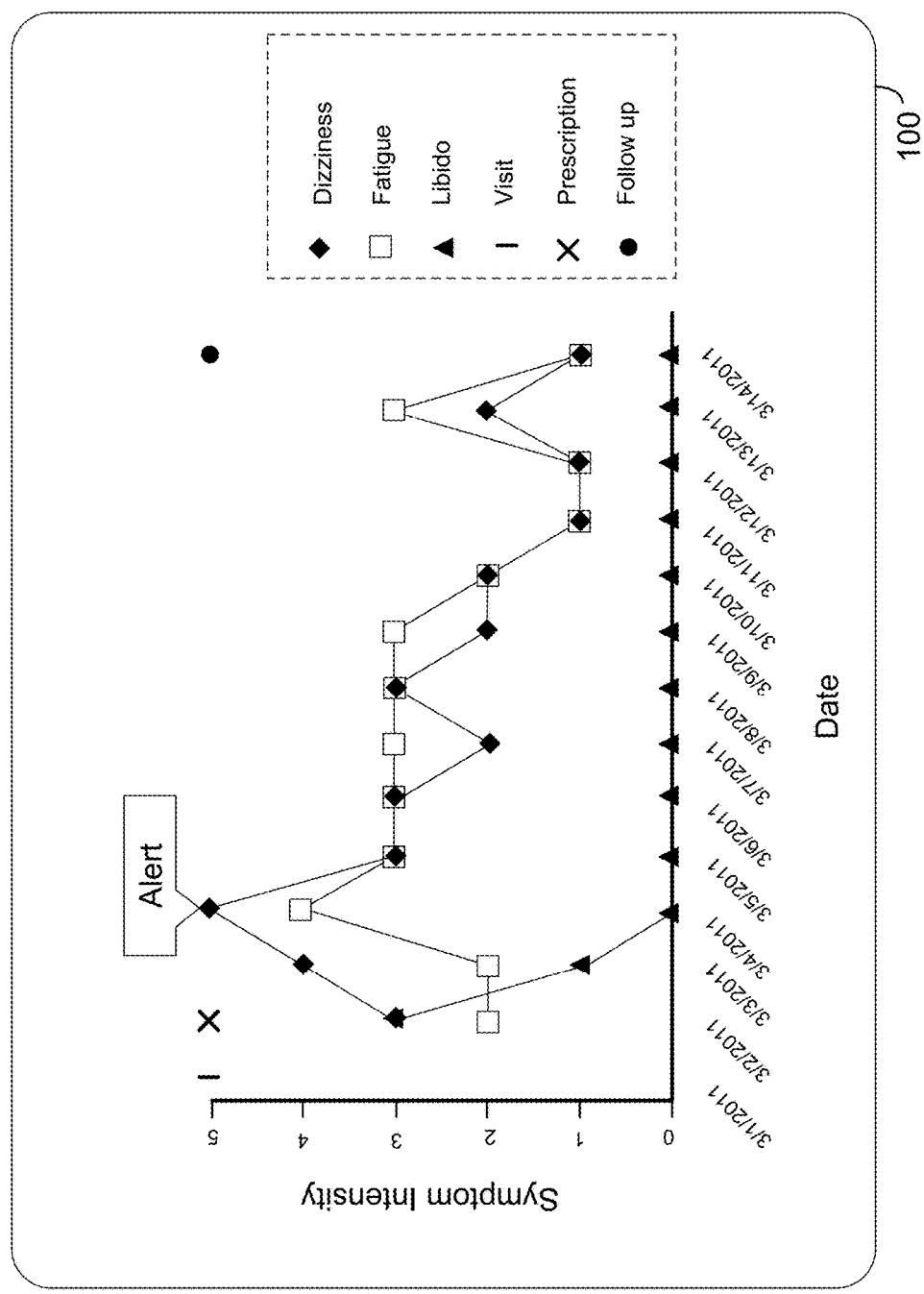
FIG. 1a illustrates a graphical display of a computing device running an example blood pressure medication tracker program, commercially known as "BPRx-Tracker", as it might appear on a medical provider's display screen at the time of consultation.

As a preliminary matter, it will readily be understood by one having ordinary skill in the relevant art ("Ordinary Artisan") that the present invention has broad utility and application. As should be understood, any embodiment may incorporate only one or a plurality of the above-disclosed aspects of the invention and may further incorporate only one or a plurality of the above-disclosed features. Furthermore, any embodiment discussed and identified as being "preferred" is considered to be part of a best mode contemplated for carrying out the present invention. Other embodiments also may be discussed for additional illustrative purposes in providing a full and enabling disclosure of the present invention. As should be understood, any embodiment may incorporate only one or a plurality of the above-disclosed aspects of the invention and may further incorporate only one or a plurality of the above-disclosed features. Moreover, many embodiments, such as adaptations, variations, modifications, and equivalent arrangements, will be implicitly disclosed by the embodiments described herein and fall within the scope of the present invention.

Accordingly, while the present invention is described herein in detail in relation to one or more embodiments, it is to be understood that this disclosure is illustrative and exemplary of the present invention, and is made merely for the purposes of providing a full and enabling disclosure of the present invention. The detailed disclosure herein of one or more embodiments is not intended, nor is to be construed, to limit the scope of patent protection afforded the present invention, which scope is to be defined by the claims and the equivalents thereof. It is not intended that the scope of patent protection afforded the present invention be defined by reading into any claim a limitation found herein that does not explicitly appear in the claim itself.

Thus, for example, any sequence(s) and/or temporal order of steps of various processes or methods that are described herein are illustrative and not restrictive. Accordingly, it should be understood that, although steps of various processes or methods may be shown and described as being in a sequence or temporal order, the steps of any such processes or methods are not limited to being carried out in any particular sequence or order, absent an indication otherwise. Indeed, the steps in such processes or methods generally may be carried out in various different sequences and orders while still falling within the scope of the present invention. Accordingly, it is intended that the scope of patent protection afforded the present invention is to be defined by the appended claims rather than the description set forth herein.

Additionally, it is important to note that each term used herein refers to that which the Ordinary Artisan would understand such term to mean based on the contextual use of such term herein. To the extent that the meaning of a term used herein—as understood by the Ordinary Artisan based on the contextual use of such term—differs in any way from any particular dictionary definition of such term, it is intended that the meaning of the term as understood by the Ordinary Artisan should prevail. Moreover, it will be appreciated that virtualization is known in some computing contexts, such as virtualization of memory and processing. Virtualization enables the abstraction of computer resources and can make a single physical resource appear, and function, as multiple logical resources. Traditionally, this capability enables developers to abstract development of an application so that it runs homogenously across many hardware platforms. Additionally, this capability enables multiple virtual machines to be created and run on a single real computer, wherein each virtual machine corresponds to a different computer including its own operating system. More generally, virtualization is geared toward hiding technical detail through encapsulation. This encapsulation provides the mechanism to support complex networking and improved security that is required to enable routine at client devices. More specifically, and as used in the incorporated references and herein, a virtual machine (sometimes referred to hereinafter as a "VM") essentially comprises a software copy of a real machine interface, and may include additional virtualization of a computer's resources—including additional interfaces for network communications, or even virtualization of a computer itself. The purpose of running a VM is to provide an environment that enables a computer to isolate and control access to its services. A virtual machine monitor (VMM) component is used to run a plurality of VMs on a real machine and to interface directly with that real machine. In a virtual dispersive routing (VDR) implementation, the VMM creates a VM for each distinct connection for a client on the computer, with the VM comprising the communication interface for making the connection. It is helpful to explain at this juncture that what comprises a connection can vary, but in general includes a transfer of data in the form of packets from a first end device to a second end device along a path (or route). It will be appreciated that a single application can require multiple connections. For example, an application may require multiple connections because of bandwidth application requirements and performance requirements; in this event each connection preferably interfaces with its own VM and the connections can utilize (sometimes referred to as being tied to) the same routing protocol or different routing protocols, even though the connections are themselves necessitated by the same application. Similarly, although two connections may at times travel along an identical path, the connections themselves are nevertheless distinct, and each will preferably still continue to interface with its own VM. The VMM creates and manages the VMs in making these connections.

Regarding applicability of 35 U.S.C. § 112, ¶6, no claim element is intended to be read in accordance with this statutory provision unless the explicit phrase "means for" or "step for" is actually used in such claim element, whereupon this statutory provision is intended to apply in the interpretation of such claim element.

Furthermore, it is important to note that, as used herein, "a" and "an" each generally denotes "at least one," but does not exclude a plurality unless the contextual use dictates otherwise. Thus, reference to "a picnic basket having an apple" describes "a picnic basket having at least one apple" as well as "a picnic basket having apples." In contrast, reference to "a picnic basket having a single apple" describes "a picnic basket having only one apple."

When used herein to join a list of items, "or" denotes "at least one of the items," but does not exclude a plurality of items of the list. Thus, reference to "a picnic basket having cheese or crackers" describes "a picnic basket having cheese without crackers", "a picnic basket having crackers without cheese", and "a picnic basket having both cheese and crackers." Finally, when used herein to join a list of items, "and" denotes "all of the items of the list." Thus, reference to "a picnic basket having cheese and crackers" describes "a picnic basket having cheese, wherein the picnic basket further has crackers," as well as describes "a picnic basket having crackers, wherein the picnic basket further has cheese."

Referring now to the drawings, one or more preferred embodiments of the present invention are next described. The following description of one or more preferred embodiments is merely exemplary in nature and is in no way intended to limit the invention, its implementations, or uses.

Figure 1B:
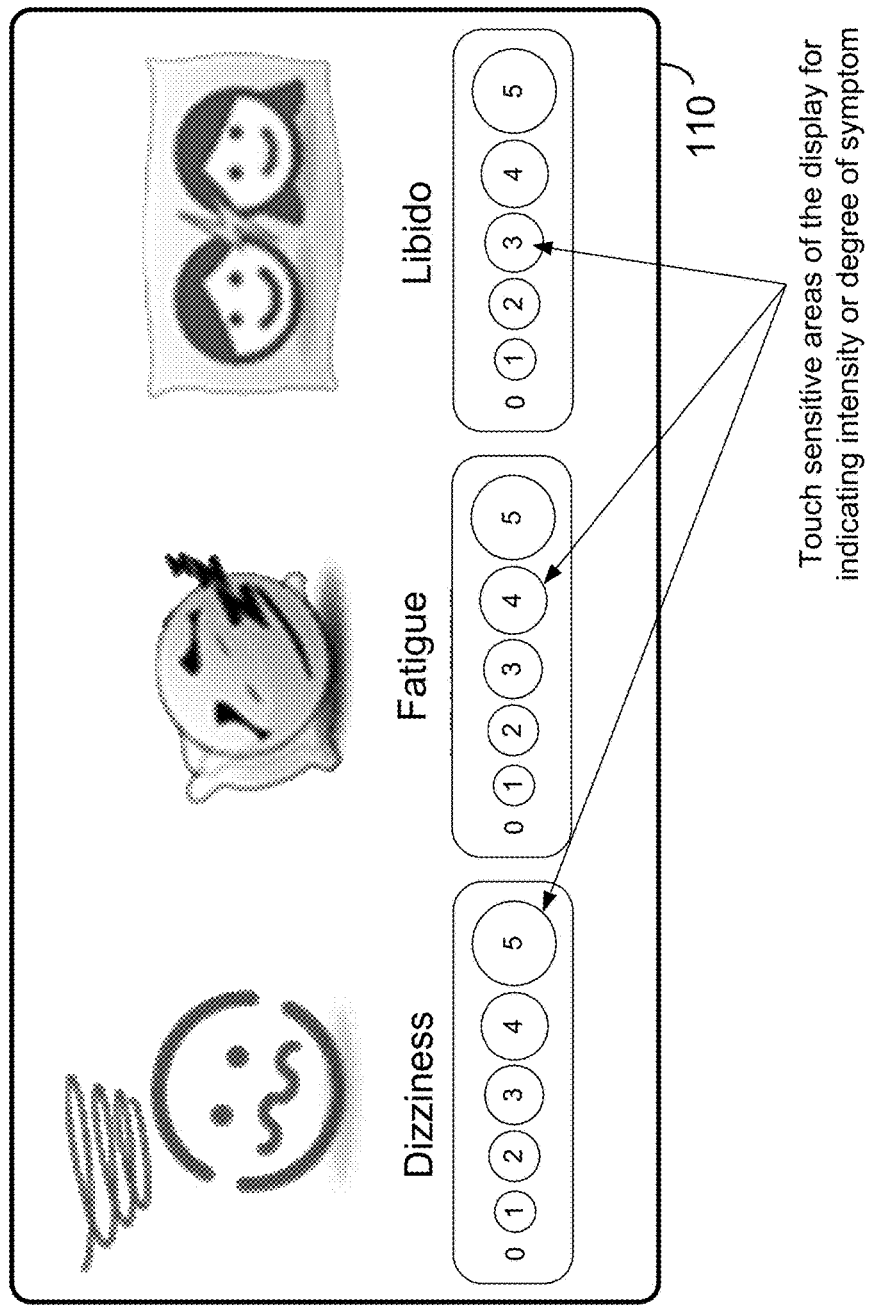
FIG. 1b illustrates an exemplary display of a computer device of a person showing a predefined set of symbolic representation of symptoms and a range of intensity of each symptom for selection by the person.

With reference now to the drawings, FIG. 1a shows a graphical display 100 of a computing device running an example blood pressure medication tracker program, commercially known as "BPRx-Tracker", as it might appear on a medical provider's display screen at the time of consultation. FIG. 1b illustrates an exemplary display 110 of a computer device of a person showing a predefined set of symbolic representation of symptoms and a range of intensity of each symptom for selection by the person, which exemplary display could have been used by a person whose history of symptoms is shown in FIG. 1a.

The example of FIG. 1a illustrates how a healthcare provider might follow symptoms that he or she is especially concerned about after prescribing a beta-blocker (blood pressure medication) at a patient visit on Mar. 1, 2011. Specifically, in this example subjective feelings (symptoms) are rated daily, beginning on Mar. 2, 2011, from 0-5 on a sliding scale. While the example uses daily as the time frame, other time frames, such as hourly or every six hours while awake, could be used as desired.

As shown in FIG. 1a, the patient filled the prescription on March 2 and started tracking his or her symptoms. He or she rapidly became dizzy to a potentially dangerous level on March 4, and the clinic was automatically notified via an alert, which may be sent for example via email or text messaging. The alert enables the clinic staff the opportunity to contact the patient to determine how the patent is doing. At a follow-up visit on Mar. 14, 2011, the patient indicated that he or she was fine; however, the prescribing physician knew from the previous data entries and resulting history shown in FIG. 1a that the patient was failing to mention the problem with his or her libido as well as the severe dizziness and fatigue experienced soon after prescribing the medication (and presumably taking the medication by the patient). This information, which otherwise would be unknown to the healthcare provider, thus is available and used in clinical decision making to, for example, alter the prescription, if appropriate; minimize adverse reactions; and enhance treatment.

An application on a computing platform such as a mobile phone, laptop computer, computing tablet (i.e., a Xoom or iPad tablet) used by the patient to record the symptoms and other observations, enables real-time gathering of information. Accessible recording of symptoms and experiences from a patient's (individual) perspective as recorded by the individual and recorded in real-time that is practical. Recording devices can be mobile phones, phones dictaphones and others. The conversations and data are time and geospatially stamped so that trends can be analyzed over time and space.

It will be appreciated from this disclosure that, to solve the literacy, general communication skills, and language, cultural, ethnic, doctor/patient and social economic barriers, a series of pictorial representations are used to allow the person to quantify his or her condition. These representations can be recognized by humans as being representative of specific symptoms, and can be entered through a variety of recording devices (visual icons, verbal sound bytes).

Figure 2B:
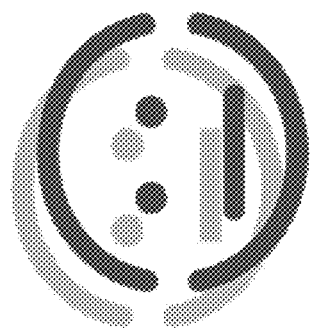
FIG. 2a through FIG. 2f illustrate some exemplary symbolic representations of symptoms, each of which could be included in a predefined set for presenting to a user for selection.
Figure 2C:
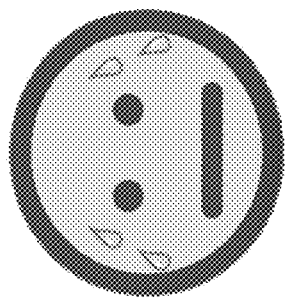
Figure 2A:
Figure 2E:
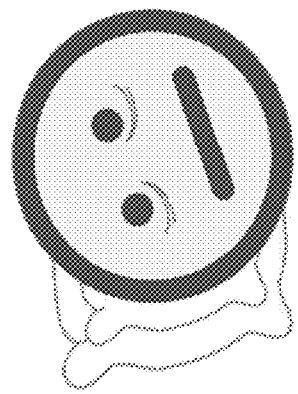
Figure 2F:
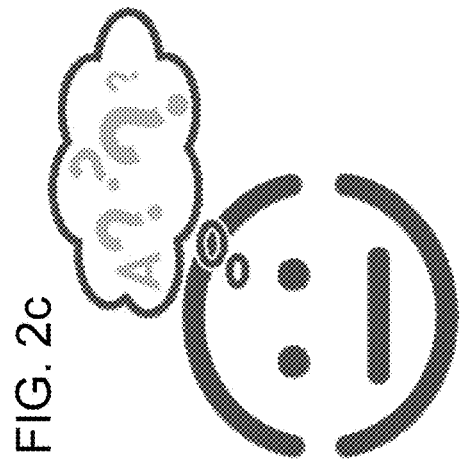
Figure 2D:
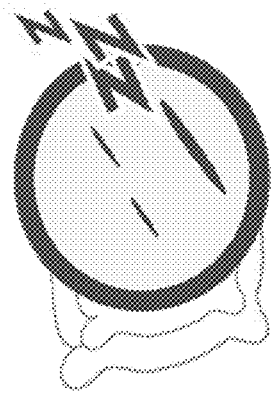
Figures 3C, 3F:
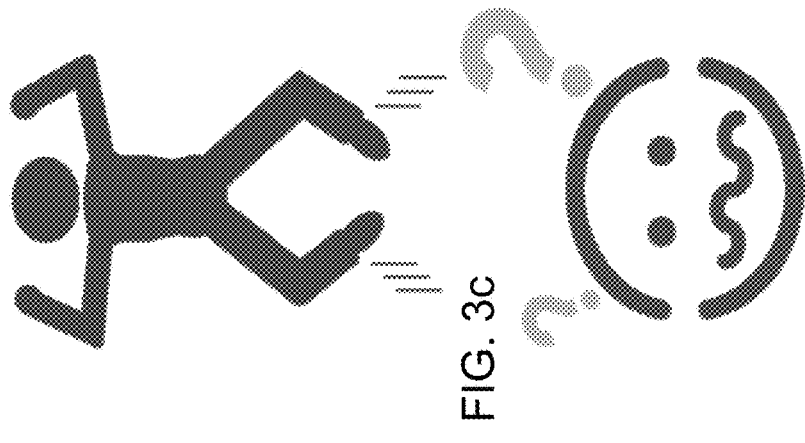
FIG. 3a through FIG. 3f illustrate additional exemplary symbolic representations of symptoms, each of which could be included in a predefined set for presenting to a user for selection.
Figure 3B:
Figure 3E:
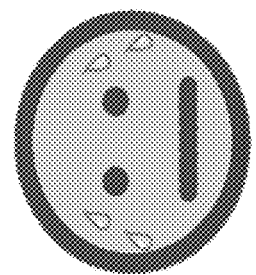
Figure 3A:
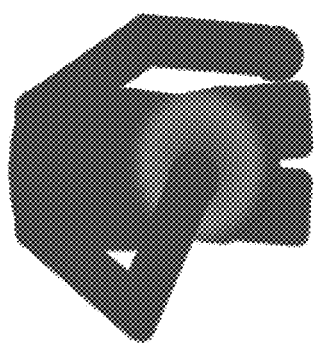
Figure 3D:
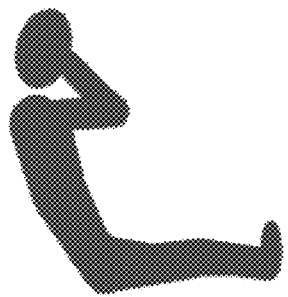

Examples of universal icons used in preferred embodiments are shown in FIG. 2a through FIG. 2f; and FIG. 3a through FIG. 3f. Specifically, FIG. 2a represents coughing; FIG. 2b represents blurred vision; FIG. 2c represents sweating; FIG. 2d represents fatigue or deep sleep (depending on context); FIG. 2e represents sleeplessness; and FIG. 2f represents forgetfulness; FIG. 3a represents generic abdominal problems (such as, for example, indigestion/heartburn); FIG. 3b represents diarrhea; FIG. 3c represents hyperactivity; FIG. 3d represents despair or fatigue; FIG. 3e represents cold sweats; and FIG. 3f represents confusion.

Symptom symbology qualities also can be captured when symptoms are selected by a person. For example, such qualities may include, in one or more preferred embodiments, anatomical region; anatomical type; discharge; runny, thick; color; volume; mood, constitutive; infective; performance; and condition clusters.

Figure 4A:
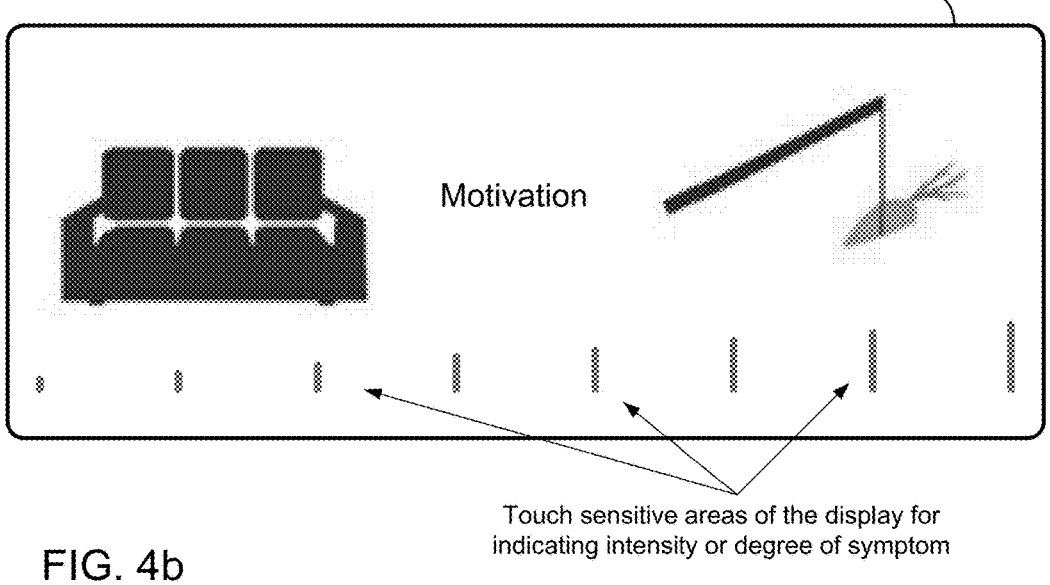
Figure 4B:
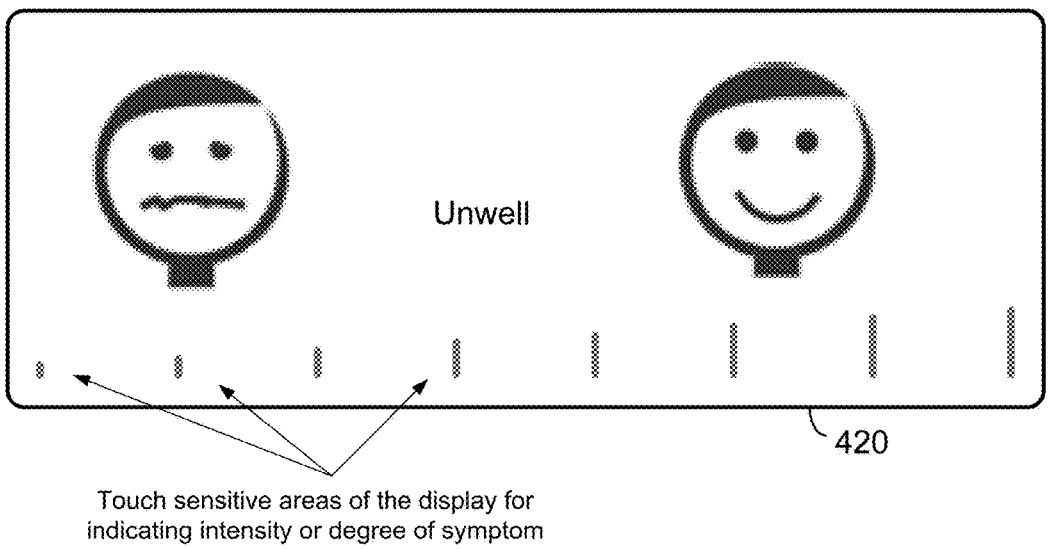
Figure 5A:
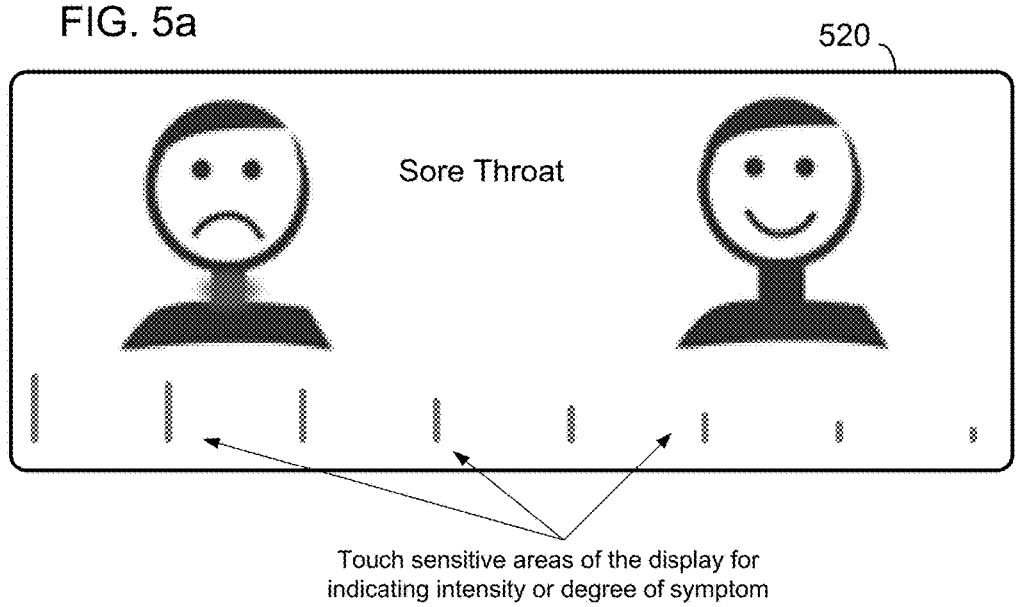
Figure 5B:
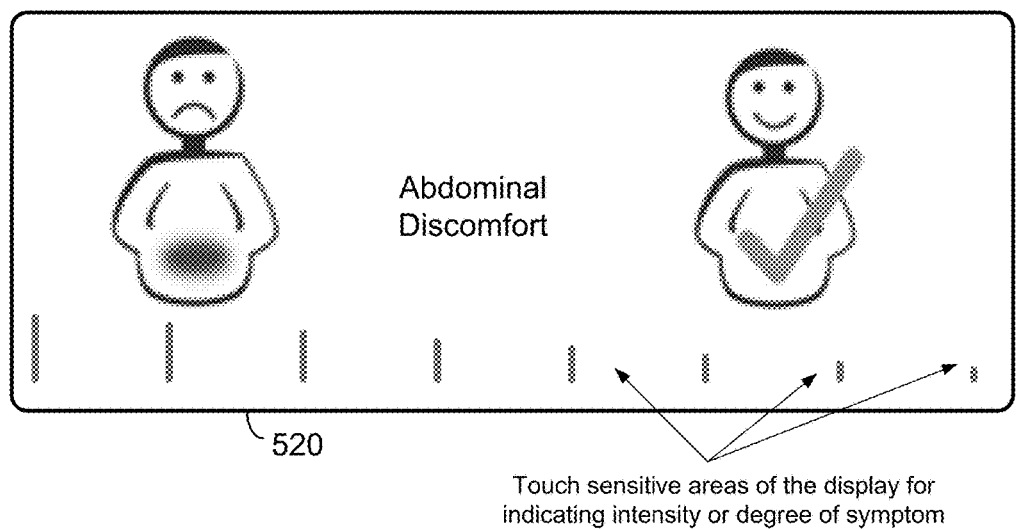

Ranges as indications of intensity of symptoms can further be used. For example, FIGS. 4a and 4b, and FIGS. 5a and 5b, each include symbolic representations wherein an intensity of each symptom can be indicated by the person while experiencing the symptom. Specifically, FIG. 4a provides for the indication by a person of the degree of motivation currently felt via a "strip" of increasing intensity (from left to right) of the touch sensitive display 410; FIG. 4b provides for the indication by a person of the degree of wellness currently felt (or degree to which a person feels unwell) via a "strip" of increasing intensity (from left to right) of the touch sensitive display 420; FIG. 5a provides for the indication by a person of the degree of sore throat currently felt via a "strip" of decreasing intensity (from left to right) of the touch sensitive display 510; and FIG. 5b provides for the indication by a person of the degree of abdominal discomfort currently felt via a "strip" of decreasing intensity (from left to right) of the touch sensitive display 520. FIG. 5c illustrates additional symbolic representations wherein an intensity of each symptom can be indicated by a person while experiencing the symptom via sliding bars of the display 530. In this example, once the appropriate indications of intensity or degree have been set by the person, the update button is selected at the bottom of the display 530.

In accordance with one or more preferred embodiments of the invention, a person selects one or more images from a predefined set of images of symptoms. Preferably the predefined set includes less than ten. The predefined set further preferably pertains to specific diseases, disease processes, or groups whereby more focused feedback and monitoring results from the symptom-tracking process. This overcomes the problem of having too many symptoms to choose from and not knowing what symptoms to report. Exemplary conditions include head injury, influenza, and asthma. Exemplary groups include athletes and those on blood pressure medication or with heart disease.

A goal of one or more aspects or features of the present invention is to enhance communications between patients and their providers. To minimize barriers, preferred embodiments of the invention utilize a single or double word (multiple language insertion capabilities) and single icon identifier of symptoms (icons are modifiable depending upon user or user group preference), linked to an intensity scale—this is automatically time-stamped and preferably associated with geolocation information as well, provided that the communications hardware includes geolocating capabilities.

It is believed that preferred embodiments of the invention represent powerful and cost-effective tools for data collection for communication, recording, auditing, and enhanced clinical decision-making through combined data display or by running decision support algorithms on the data.

For example, with reference to FIG. 1*a*, each symptom entry is a useful data point that, when combined with other data (biometrics, location, other symptom entries) inform on population, sub-population and individual behaviors.

It is also preferred that, for persons who are blind, the device include a piezoelectric component, or other heat generating component, which heat can be substituted for light in order to simulate virtual Braille functionality.

Medical SAN Preferably Utilizing Virtual Dispersive Routing

Additionally, in one or more preferred implementations, storage area network technology and/or virtual dispersive routing technology, also preferably including VDR servers (as described in documents incorporated by reference hereinabove), are utilized in the above medical context to provide secure storage and access to medical records and data.

A storage area network (SAN) is a network created to interconnect one or more data storage devices, e.g. different forms of data storage devices, with one or more servers. In a conventional implementation of a SAN, cloud-based storage and processing are utilized. However, the use of such cloud-based storage and processing can present significant security and information fidelity issues. For example, data to be transferred may not transfer due to an error with a server or a storage device, or a hacker may attempt to break in through a public access point, such as a website. Further, breaches may occur when employees are careless or malicious, thereby allowing data to be copied or stolen from a database, or, perhaps worse, allowing data to be changed, or other actions taken that may case additional harm. Further still, sometimes a storage area network may fail to transfer files because only one route is available, which can increase risk if communications are attempted multiple times. Encryption is sometimes utilized to protect data in a SAN, but, given enough processing power, such encryption alone may not be enough.

Thus, storing information in a network, such as in cloud storage, is subject to theft and hacking, both where information is stored and as it is being transferred over the network.

In one or more preferred implementations, virtual dispersive routing technology (as disclosed in documents which are incorporated herein by reference above) is utilized in a storage context to form one or more dispersive SANs.

In an exemplary preferred implementation of a dispersive SAN, data is dispersed for secure storage by being distributed to, and stored at, a plurality of devices, and virtual dispersive routing is utilized to effect such dispersed distribution of data. For example, data may be dispersed, via virtual dispersive routing, from a mobile phone and stored at a laptop, a desktop, another mobile phone, and a server. Thus, data may be distributed to multiple, physically separate places. Hacking such data at its place of storage would thus require hackers to hack multiple different devices at multiple, different sites to gather all of the data.

Similarly, as the data is distributed utilizing virtual dispersive routing, multiple routes would have to be hacked to gather all of the data. Further, the security functionality of virtual dispersive routing described in the incorporated documents would render hacking of transferred data more difficult.

With respect to accessing data, a device 650 accessing data preferably receives a plurality of data streams from each of the devices 652,654,656,658 on which any portion of the data is stored using virtual dispersive routing. Such communications could occur over, for example, a public network, a private network, a wireless personal area network (WPAN), or a wireless local area network (WLAN). Preferably, the gaps between packets are controlled by virtual machine messaging so that timing of packets can be used as another mechanism to determine hacking, rerouting and other network attack techniques. Similarly, the sequence of data from each source and size of data transmitted is controlled by virtual machines, and by streaming data simultaneously from multiple sites, hacking can be further frustrated. By placing a signal on either side of a connection, virtual machines can signal to each other which route is the fastest and stripe data to be encoded across multiple sites. Further, direct connection between devices enables more efficient communications (e.g., with less overhead) and faster communications, and further obviates the need for authentication and data transfer via a server, unless an specific software application running on one of the devices specifies the use of authentication and data transfer via a server.

In dividing storage of data across multiple devices, in at least some implementations some storage overlap may be utilized in that some, or all, portions of data may be stored at multiple devices, so that if one device is offline such data may still be accessible from another device. Preferably, decisions on whether to send data can be directed by a client based on the presence of devices available to participate in an information transfer. Preferably, virtual machine messaging is utilized to keep track of communications to ensure quality of service and the ability to abstract networking from an application.

In at least some preferred implementations, remote storage devices are utilized for storage in a manner similar to how hard drives might be utilized in a redundant array of independent disks (RAID). Such remote storage devices might be utilized in a manner akin to any standard level of RAID, or even more exotic flavors of RAID, and even in a manner akin to nested RAID.

Thus, as described hereinabove, virtual dispersive routing can be utilized to form dispersive storage area networks (SANs), and such dispersive SANs can be utilized in a medical context to provide access to medical records and data stored at disparate dispersed locations.

For example, several hospitals (and doctor's offices, etc.) in a region may each have their own servers with medical records, and other data, stored thereon. In a preferred implementation, users would be able to access medical records stored at any hospital's server via virtual dispersive routing. Further, in at least some preferred implementations, medical records may be segmented and dispersed to multiple physical servers, or devices, for enhanced security or redundancy, as described hereinabove with reference to dispersive SANs, and in documents incorporated herein.

Preferably, such a system allows for the sharing of medical information while retaining storage of the information at its current location, e.g., a doctor's office storing patient records would not have to cede storage of such patient records to a central server or database just to ensure available access thereto by other users. Thus, as data can remain stored where it currently is, in some preferred implementations, no additional server or database infrastructure is needed to consolidate medical records or data.

Moreover, to address internal security issues, a dispersed SAN is used to enable specific access to certain segments of the data. By distributing data across multiple servers and only giving access to specific servers, information can be kept secure (servers can be physically located in different locations, separate physical devices or separated by virtual machines) and the ability to copy the information from the servers becomes impossible from a single site. To be able to maintain anonymity for researching medical information, certain fields can be separated from the data (i.e. name and address). A reference number is used in the record to identify and to reassemble the complete record. The networking virtual machines are given information on how to access the data. The access control determines which set of records a user has access to.

Figure 6A:
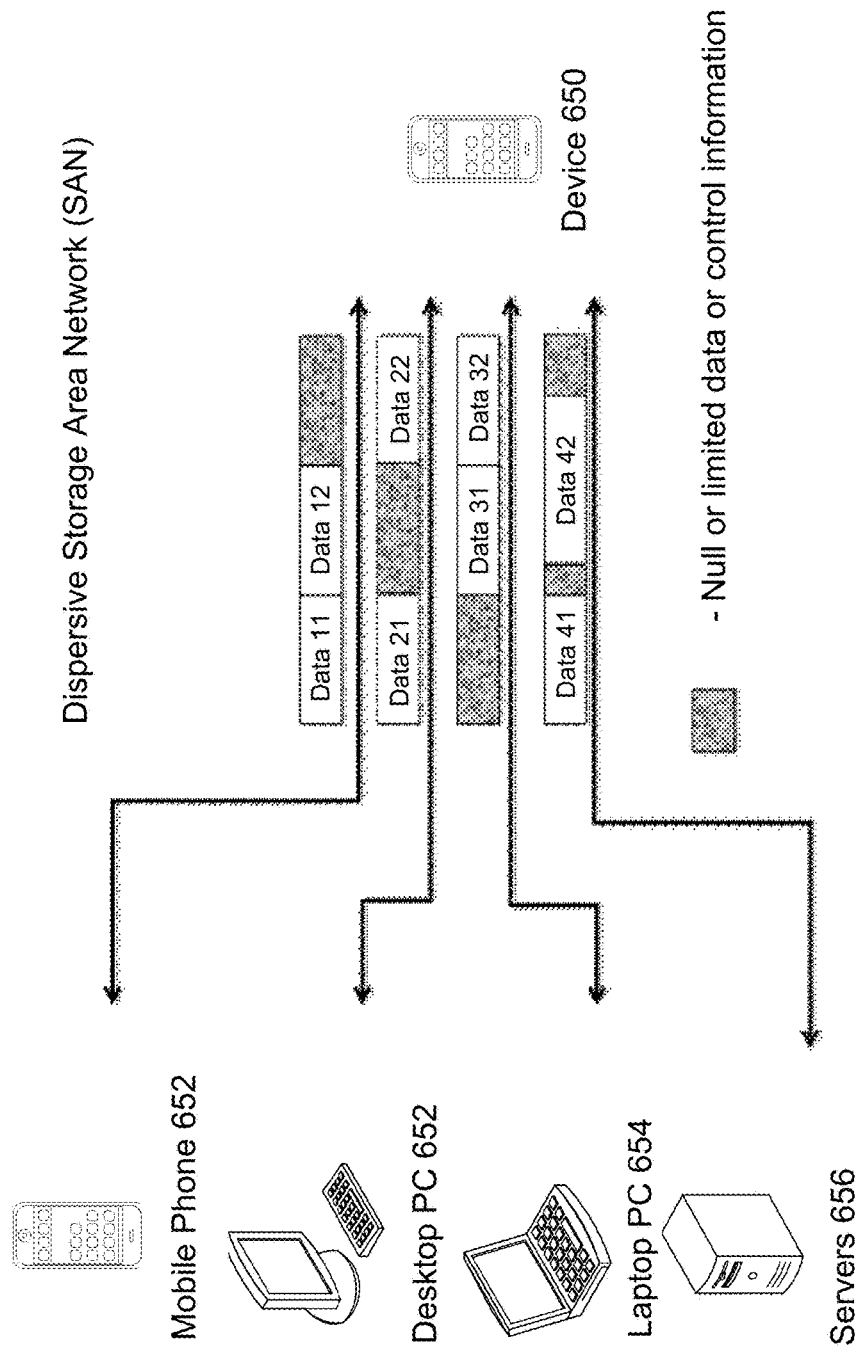
Figure 6B:
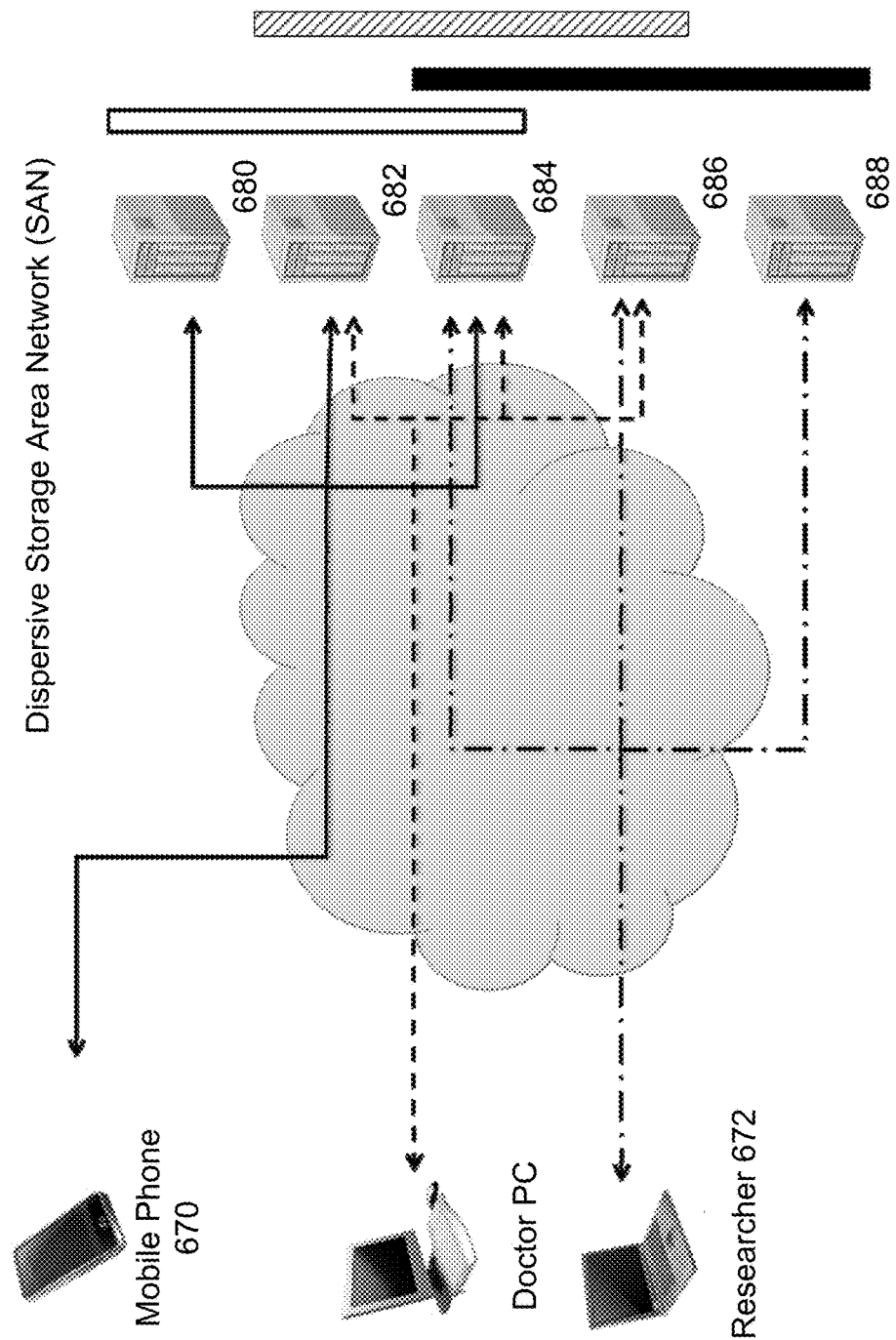
FIG. 6b illustrates a high level system architecture utilizing dispersive data storage servers in a storage area network (SAN).

For example, with reference to FIG. 6B, a user's mobile phone 670 is allowed to access specific information that is "proper" for the user to access. In this example, the user would be restricted to the servers 680,682,684 indicated by the white bar (that is, the top three servers). Similarly, a Researcher 672 is blocked from accessing certain information so he or she is only able to access the servers 684,686, 686 indicated by the black bar (that is, the bottom three servers). A doctor would have access to the servers 682,684, 686 indicated with a cross-hatched bar (that is, the middle three servers). In some preferred implementations, information can be duplicated on multiple servers and/or specific fields can be removed to improve privacy. The sites, where the information is stored, are encoded on a user device. To deter hacking and impersonation attacks (such as man-in-the-middle), a VM (Virtual Machine) can open separate simultaneous connections to each storage device (examples of storage devices are servers, desktop computers, mobile phones and other computing devices present on the network). To leverage Virtual Dispersive Networking (VDN), a server can use a VM to control networking. The use of VDN would enable deflection of routing through other servers and clients using SWRT (SoftWare RouTer).

Additionally, the data on the client devices (mobile phone, Doctor's PC and Researcher) can be backed up using standard backup methods.

Finally, it will be appreciated that while the client devices can also leverage the dispersive SANs techniques, too, and this example has been described utilizing virtual dispersive routing, it nevertheless is contemplated that the medical data could be stored and accessed in a non-dispersive SAN with the data segregation described above. User of dispersive routing, however, is preferred for security and privacy.

Medical Decision Making Algorithms

In one or more preferred embodiments, the medical data and, specifically, the data acquired from the aforementioned symptom tracking apparatus, methods and systems, is used in decision making. Moreover, the medical decision making algorithms preferably are based on (i.e., take into account) how the data is acquired. For instance, the data can be acquired based on individual-to-machine inputs, where the machine is typically a computer but may be any communication device such as a telephone, a voice recorder, or a display interface. This method of data input has the potential to produce cleaner, more valid data, thereby overcoming problems with the traditional doctor-to-patient-to-computer-records approach that has potential for data corruption from poor or inaccurate recall (patient memory), communication barriers, translation, and transcription. Therefore, the data that the decision-making algorithms are based on from the aforementioned symptom tracking apparatus, methods and systems is believed to be more robust and should lead to improvements in clinical decision support.

Additionally, it is contemplated within certain aspect and features of the invention that direct patient input of each data point may be (and preferably is) assigned different weighting for consideration in the decision making process. In this respect, there is a user defined (intrinsic) weight that the user assigns when entering the data. This weight changes with each input. There are other algorithm defined (extrinsic) weights. The intrinsic weight for each data point is fixed whereas the extrinsic weights are fluid and dependent on the decision-making environment. The extrinsic weight of a data point is determined by a variety of factors including, for example: temporal band; geographical band; related diagnostic group; demographic band; community band, where community can include relatives, contacts, friends, colleagues and so on; potential for danger, "red flag" assignment; past history; family history; intake—food, drink, supplements; pharmaceutical or drugs—prescribed, over-the-counter, recreational; activity; diagnoses; and interventions.

Dataset categories in accordance with one or more preferred embodiments include: minimal (most efficient); confusing (contains corrupt or invalid data); and inadequate.

Data quality in accordance with one or more preferred embodiments also is assigned and, in particular, each data point is assigned a data quality rank. An example would be a new user for an input device would have earlier inputs with a lesser ranking compared to later inputs that would have a higher data point ranking.

As disclosed hereinabove, each data point also preferably is time-stamped at the time of the input, which preferably corresponds with the time of the "real experience". Moreover, if different, the person could additionally indicate the time of the real experience. For example, for a meal that was ingested at midday and entered at 1:00 pm, both a 1:00 pm timestamp could be recorded as well as data indicating that the meal was eaten at noon.

Preferably each data point is also stamped for where the data was entered and, potentially, for where the data point was accrued. For example, someone who developed a rash while walking through a field of flowers at 1:30 pm may enter the data at 1:50 pm at a different location. The entry location is preferably always recorded automatically by the device provided there is a location function, such as GPS, on the device. Additionally, with less quality ranking the user could manually enter the geographical location where he was walking, though this would preferably receive a lower quality ranking than a machine accrued stamp.

Figure 7:
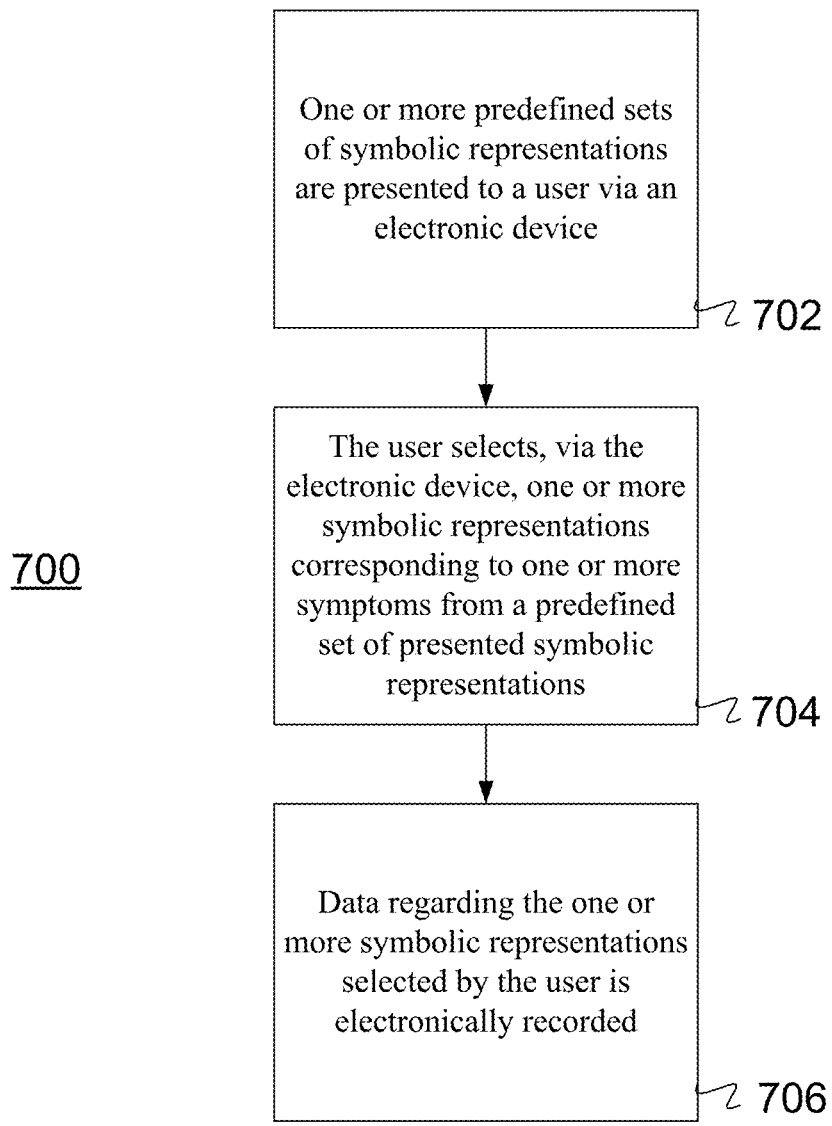
FIG. 7 illustrates an exemplary methodology in accordance with one or more preferred implementations.

FIG. 7 illustrates an exemplary methodology 700 in accordance with aspects and features described herein. As illustrated in FIG. 7, one or more predefined sets of symbolic representations first are presented 702 to a user via an electronic device. Thereafter, the user selects 704, via the electronic device, one or more symbolic representations corresponding to one or more symptoms from a predefined set of presented symbolic representations. Subsequently, data regarding the one or more symbolic representations selected by the user is electronically recorded 706.

This methodology can be repeated for repeated electronic recordation of data regarding selected symbolic representations, for example by the same user with the same mobile device (or a different mobile device) over days, weeks, months, or years, as well as by other users.

Figure 8:
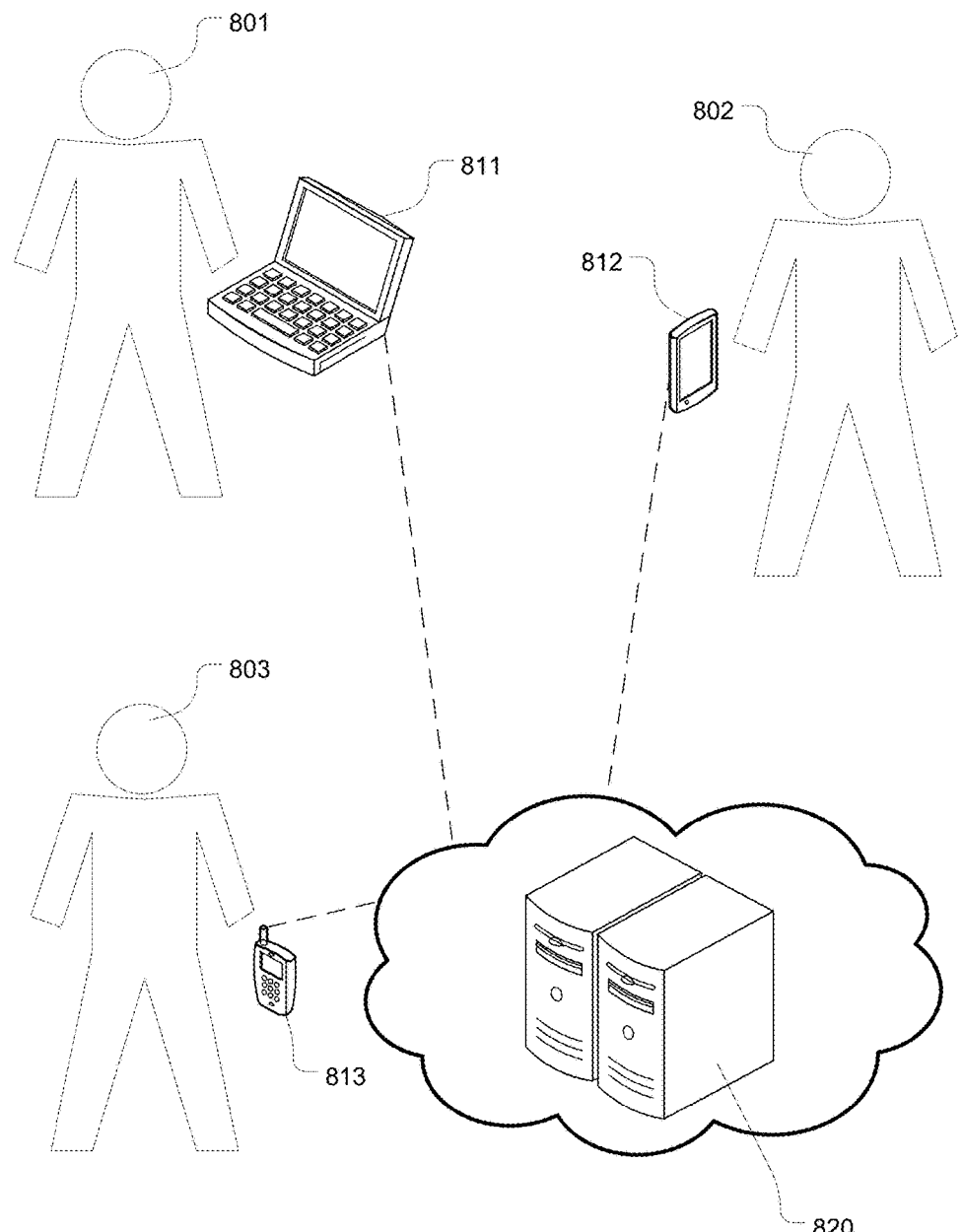
FIG. 8 illustrates an exemplary system which can be utilized with the methodology of FIG. 7.

FIG. 8 illustrates an exemplary system which can be utilized with such methodology. In this system, a plurality of users 801,802,803 can select symbolic representations using respective electronic devices 811,812,813. Data regarding the one or more symbolic representations selected by such users can be electronically recorded at one or more servers 820. Utilizing such recorded data, symptoms of users who have entered data can be monitored.

Figure 9:
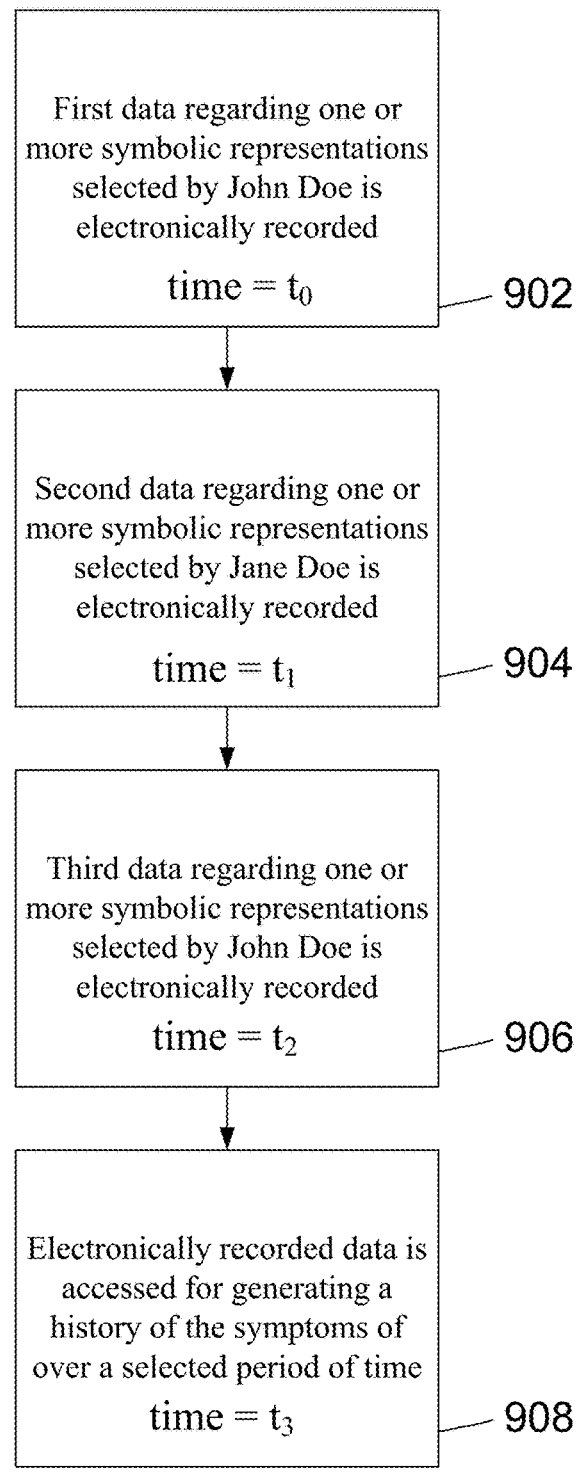
FIG. 9 illustrates a exemplary methodology for monitoring symptoms of users who have entered data via the methodology of FIG. 7.

For example, consider a scenario as illustrated in FIG. 9 in which first data regarding one or more symbolic representations selected 902 by John Doe is electronically recorded at time equal to $t_0$, second data regarding one or more symbolic representations selected 904 by Jane Doe is electronically recorded time equal to $t_1$, and third data regarding one or more symbolic representations selected 906 by John Doe is electronically recorded time equal to $t_2$. Thereafter, at time equal to $t_3$ this recorded data is accessed 908 and a report is generated of a history of symptoms for this particular user, John Doe, over a selected period of time including from time $t_0$ to $t_2$, from time $t_0$ to $t_1$, from time $t_1$ to $t_2$, as desired. Expanding upon this example, rather than selecting a single user, a set of users (representing a subset of users) may be selected and a history generated for the plurality of users.

It is believed that several benefits of one or more preferred embodiments of the invention include: the enablement of people to put their symptoms into a computing device regardless of literacy; the enablement of data to be recorded in real-time or near real-time regardless of literacy; the spreading out (or dispersing) of data in order to improve security and provide anonymity for individuals (i.e. patients); the reduction in the opportunity for misremembering or forgetting important facts; the provision of a solution for people regardless of their literacy, general communication skills, and language, cultural, ethnic, doctor/patient and social economic barriers, minimizing data corruption due to translation and transcription errors; the reduction in the opportunities for data to be stolen at the storage site; the improvement of security of the access of data; and the enhanced medical decision making.

Based on the foregoing description, it will be readily understood by those persons skilled in the art that the present invention is susceptible of broad utility and application. Many embodiments and adaptations of the present invention other than those specifically described herein, as well as many variations, modifications, and equivalent arrangements, will be apparent from or reasonably suggested by the present invention and the foregoing descriptions thereof, without departing from the substance or scope of the present invention. Accordingly, while the present invention has been described herein in detail in relation to one or more preferred embodiments, it is to be understood that this disclosure is only illustrative and exemplary of the present invention and is made merely for the purpose of providing a full and enabling disclosure of the invention. The foregoing disclosure is not intended to be construed to limit the present invention or otherwise exclude any such other embodiments, adaptations, variations, modifications or equivalent arrangements, the present invention being limited only by the claims appended hereto and the equivalents thereof.

What is claimed is:

1. A method for storing and accessing data in a dispersive storage area network (SAN) comprising an electronic device having a network interface and software loaded on the electronic device configured to spawn a plurality of respective virtual machines that each virtualizes network capabilities of the network interface such that a respective virtual network connection is provided; and a plurality of storage devices, each storage device having data stored thereon representing a portion of stored information, each storage device being associated with a user access level, and each storage device having software loaded thereon configured to spawn a plurality of respective virtual machines that each virtualizes network capabilities of that storage device such that a respective virtual network connection is provided, the method comprising:
  (a) storing, at each of the plurality of storage devices, information from the electronic device by
    (i) breaking up, at the electronic device, the information into a plurality of portions, each of one or more portions of the plurality of portions being associated with a respective user access level,
    (ii) spawning, at the electronic device, a plurality of virtual machines that each virtualizes network capabilities of the network interface such that a respective virtual network connection is provided, and
    (iii) storing each respective portion of the plurality of portions at a respective storage device of the plurality of storage devices, including storing each of the one or more portions at a respective one of the storage devices which is associated with the same respective user access level as that portion, such storing comprising, for each respective portion,
      (A) communicating, from the electronic device using one of the provided virtual network connections, data packets containing the respective portion of the information to the respective storage device,
      (B) receiving, at a virtual machine of the respective storage device, the respective portion, and
      (C) storing, at the respective storage device, the respective portion; and
  (b) thereafter accessing, by another electronic device operated by a user having a first user access level, some of the stored information by accessing a first set of portions of the plurality of portions, each portion of the first set of portions being associated with the first user access level, such accessing of some of the stored information comprising
  (i) spawning, at the electronic device, a plurality of virtual machines that each virtualizes network capabilities of the network interface such that a respective virtual network connection is provided,
  (ii) receiving, at each of the spawned virtual machines of the electronic device, data packets communicated by a respective storage device of the plurality of storage devices which is associated with the first user access level using a respective virtual network connection provided by a virtual machine of that storage device, the received data packets containing data representing one of the portions of the information, and
  (iii) assembling the data received at each of the spawned virtual machines of the electronic device into the accessed information;
(c) wherein data in at least some portions of the plurality of portions is redundant to other data in the at least some portions of the plurality of portions such that the stored information can be reassembled even if data is not received from all of the storage devices of the plurality of storage devices;
(d) wherein one of the spawned virtual machines of the electronic device comprises virtualization of a real machine interface of the electronic device; and
(e) wherein the method provides a technical solution to the technical problem of securely storing data over a network which involves distributing data across multiple networked storage devices utilizing virtual network connections, and selectively providing users access to data stored on the networked storage devices utilizing virtual network connections, where the selective access is based on whether an access level of a user matches an access level of a networked storage device.

2. The method of claim 1, wherein one of the spawned virtual machines of the electronic device includes additional virtualization of one or more additional resources of the electronic device.

3. The method of claim 1, wherein one of the spawned virtual machines of the electronic device comprises virtualization of the electronic device itself.

4. The method of claim 1, wherein one of the spawned virtual machines of one of the storage devices comprises virtualization of a real machine interface of such storage device.

5. The method of claim 1, wherein one of the spawned virtual machines of one of the storage devices comprises virtualization of a real machine interface of such storage device, and further includes additional virtualization of one or more additional resources of the electronic device.

6. The method of claim 1, wherein one of the spawned virtual machines of one of the storage devices comprises virtualization of such storage device itself.

7. A method for storing and accessing data in a dispersive storage area network (SAN) comprising an electronic device having a network interface and software loaded on the electronic device configured to spawn a plurality of respective virtual machines that each virtualizes network capabilities of the network interface such that a respective virtual network connection is provided; and a plurality of storage devices, each storage device having data stored thereon representing a portion of stored medical information, each storage device being associated with a user access level, and each storage device having software loaded thereon configured to spawn a plurality of respective virtual machines that each virtualizes network capabilities of that storage device such that a respective virtual network connection is provided, the method comprising:
(a) storing, at each of the plurality of storage devices, medical information from the electronic device by
  (i) breaking up, at the electronic device, the medical information into a plurality of portions, each of one or more portions of the plurality of portions being associated with a respective user access level,
  (ii) spawning, at the electronic device, a plurality of virtual machines that each virtualizes network capabilities of the network interface such that a respective virtual network connection is provided, and
  (iii) storing each respective portion of the plurality of portions at a respective storage device of the plurality of storage devices, including storing each of the one or more portions at a respective one of the storage devices which is associated with the same respective user access level as that portion, such storing comprising, for each respective portion,
    (A) communicating, from the electronic device using one of the provided virtual network connections, data packets containing the respective portion of the medical information to the respective storage device,
    (B) receiving, at a virtual machine of the respective storage device, the respective portion, and
    (C) storing, at the respective storage device, the respective portion; and
(b) thereafter accessing, by another electronic device operated by a user having a first user access level, some of the stored medical information by accessing a first set of portions of the plurality of portions, each portion of the first set of portions being associated with the first user access level, such accessing of some of the stored medical information comprising
  (i) spawning, at the electronic device, a plurality of virtual machines that each virtualizes network capabilities of the network interface such that a respective virtual network connection is provided,
  (ii) receiving, at each of the spawned virtual machines of the electronic device, data packets communicated by a respective storage device of the plurality of storage devices which is associated with the first user access level using a respective virtual network connection provided by a virtual machine of that storage device, the received data packets containing data representing one of the portions of the medical information, and
  (iii) assembling the data received at each of the spawned virtual machines of the electronic device into the accessed medical information;
(c) wherein data in at least some portions of the plurality of portions is redundant to other data in the at least some portions of the plurality of portions such that the stored medical information can be reassembled even if data is not received from all of the storage devices of the plurality of storage devices;
(d) wherein one of the spawned virtual machines of the electronic device comprises virtualization of a real machine interface of the electronic device; and
(e) wherein the method provides a technical solution to the technical problem of securely storing data over a network which involves distributing data across multiple networked storage devices utilizing virtual network connections, and selectively providing users access to data stored on the networked storage devices utilizing virtual network connections, where the selective access is based on whether an access level of a user matches an access level of a networked storage device.

8. The method of claim 7, wherein the electronic device is located at a first location, and each of the storage devices is located at a location remote from the first location.

9. The method of claim 8, wherein the electronic device is located at a first medical facility.

10. The method of claim 9, wherein one of the storage devices is disposed at a second medical facility.

11. The method of claim 9, wherein the method further comprises displaying, at the electronic device, one or more symbolic representations corresponding to one or more symptoms from a predefined set of symbolic representations, receiving user input corresponding to a selection of one or more symbolic representations of the predefined set, and storing the selection in the dispersive SAN as part of the stored medical information.

12. The method of claim 7, wherein one of the spawned virtual machines includes additional virtualization of one or more additional resources of the electronic device.

13. The method of claim 7, wherein one of the spawned virtual machines of the electronic device comprises virtualization of the electronic device itself.

14. The method of claim 7, wherein one of the spawned virtual machines of one of the storage devices comprises virtualization of a real machine interface of such storage device.

15. The method of claim 7, wherein one of the spawned virtual machines of one of the storage devices comprises virtualization of a real machine interface of such storage device, and further includes additional virtualization of one or more additional resources of the electronic device.

16. The method of claim 7, wherein one of the spawned virtual machines of one of the storage devices comprises virtualization of such storage device itself.

17. The method of claim 7, wherein the stored medical information represents patient medical records.

18. The method of claim 17, wherein patient name and address information of a patient is stored in a first portion that is different from a second portion in which other information of the patient is stored, and wherein the assembling of the data received at each of the spawned virtual machines of the electronic device into the stored medical information utilizes a reference number that is associated both with the patient name and address information stored in the first portion, and with the other information of the patient stored in the second portion.

* * * * *